United States Patent
Lee et al.

(10) Patent No.: US 11,656,312 B2
(45) Date of Patent: May 23, 2023

(54) METHOD FOR CORRECTING MAGNETIC RESONANCE IMAGING ERROR USING HEART RATE INTERVAL

(71) Applicant: PHANTOMICS Inc., Seoul (KR)

(72) Inventors: Song Yi Lee, Seoul (KR); Jae Yoon Shim, Hanam-si (KR)

(73) Assignee: PHANTOMICS INC., Seoul (KR)

( * ) Notice: Subject to any disclaimer, the term of this patent is extended or adjusted under 35 U.S.C. 154(b) by 0 days.

(21) Appl. No.: 17/464,864

(22) Filed: Sep. 2, 2021

(65) Prior Publication Data
US 2022/0065966 A1    Mar. 3, 2022

(30) Foreign Application Priority Data

| Sep. 3, 2020 | (KR) | 10-2020-0112210 |
| Jul. 8, 2021 | (KR) | 10-2021-0089464 |
| Aug. 30, 2021 | (KR) | 10-2021-0114562 |

(51) Int. Cl.
| G01R 33/56 | (2006.01) |
| A61B 5/024 | (2006.01) |
| G01R 33/58 | (2006.01) |
| G01R 33/50 | (2006.01) |

(52) U.S. Cl.
CPC ......... *G01R 33/5608* (2013.01); *A61B 5/024* (2013.01); *G01R 33/50* (2013.01); *G01R 33/586* (2013.01)

(58) Field of Classification Search
CPC .. G01R 33/50; G01R 33/5608; G01R 33/586; A61B 5/024
See application file for complete search history.

(56) References Cited

U.S. PATENT DOCUMENTS

| 2012/0078084 A1* | 3/2012 | Piechnik | G01R 33/50 600/413 |
| 2015/0123659 A1* | 5/2015 | Weingartner | G01R 33/50 324/309 |
| 2019/0328310 A1* | 10/2019 | Robson | G01R 33/5608 |

FOREIGN PATENT DOCUMENTS

KR    10-2020-0004121 A    1/2020

OTHER PUBLICATIONS

Office Action dated Feb. 17, 2023, issued in counterpart Korean Patent Application No. 10-2021-0114562. (17 pages).

(Continued)

*Primary Examiner* — Gregory H Curran
(74) *Attorney, Agent, or Firm* — WHDA, LLP

(57) ABSTRACT

A method for correcting a magnetic resonance imaging error using a heart rate interval may include: measuring T1 of a stand-alone phantom for correcting the error; obtaining a T1 map generated by mapping a recovery time according to a reference recovery rate of protons in heart tissues of a subject inverted by a radio frequency (RF) pulse in pixel units into a two-dimensional space; calculating a correction function based on the measured T1 of the phantom; and correcting an error of the T1 map based on the calculated correction function.

14 Claims, 4 Drawing Sheets

(56) References Cited

OTHER PUBLICATIONS

Antlanger, M. et al., "Impact of Systemic Volume Status on Cardiac Magnetic Resonance T1 Mapping", Scientific Reports, http://www.nature.com/scientificreports, pp. 1-9, Apr. 3, 2018. (9 pages).
Captur, G. et al., "T1 mapping performance and measurement repeatability: results from the multi-national T1 mapping standardization phantom program (T1MES)", Journal of Cardiovascular Magnetic Resonance https://doi.org/10.1186/S12968-020-00613-3, pp. 1-17 (2020). (17 pages).

* cited by examiner

METHOD FOR CORRECTING MAGNETIC RESONANCE IMAGING ERROR USING HEART RATE INTERVAL

CROSS-REFERENCE TO RELATED APPLICATION(S)

This application claims benefit of priorities to Korean Patent Application No. 10-2020-0112210 filed on Sep. 3, 2020, Application No. 10-2021-0089464 filed on Jul. 8, 2021 and Application No. 10-2021-0114562 filed on Aug. 30, 2021 in the Korean Intellectual Property Office, the disclosures of which are incorporated herein by reference in its entirety.

BACKGROUND

1. Field

The present invention relates to a method for correcting a magnetic resonance imaging error using a heart rate.

2. Description of Related Art

Among various molecular imaging techniques, magnetic resonance imaging (MRI) has been considered as one of the most powerful and non-invasive diagnostic means because it may provide a very excellent anatomical image based on an interaction between molecules surrounding a tissue lattice and a hydrogen atom (proton).

Recently, magnetic resonance imaging techniques capable of quantitatively measuring biophysical quantities as well as existing anatomical tomographic images have been developed. Representative examples of the biophysical quantities that may be measured in the MRI include a self-recovery time of hydrogen atoms according to a high-frequency pulse, a blood flow velocity, diffusion, perfusion, and the like, in a human tissue, and may be non-invasively, safely, and accurately measured.

A contrast between tissues may be created through features for each component of self-recovery among them, and a difference in such a recovery time have been actively utilized as a biophysical quantity that may quantitatively evaluate the disease of the tissue at a molecular level.

However, an error in a result may occur according to an installation environment of a magnetic resonance imaging apparatus, a magnetic resonance imaging condition, and the like.

Conventionally, in order to correct such an error, a method (Korean Patent Laid-Open Publication Nos. 10-2018-0077181 and 10-2019-0025102) for attaching an attachable phantom to a patient, simultaneously photographing the phantom and the patient in the MRI, and correcting a measurement error of a T1 value measured in the myocardium using a T1 value measured in the phantom have been used.

A conventional method for correcting an error has a disadvantage that a position of the patient's heart should be accurately known in order to photograph the patient and the phantom together and the position of the patient's heart should be positioned on the same photographing plane as the attachable phantom in order to accurately correct the error.

For this reason, a conventional method for correcting T1 of the myocardium using the attachable phantom has a problem that a success rate is lower than an expectation in a case where it is applied to an actual clinical environment.

SUMMARY

An object of the present invention is to propose a method for correcting a T1 measurement error of a magnetic resonance imaging (MRI) system using a general type of stand-alone phantom instead of a method for correcting T1 of the myocardium using an attachable phantom.

Another object of the present invention is to propose a method for correcting a magnetic resonance imaging error using a heart rate interval.

According to an aspect of the present invention, a method for correcting a magnetic resonance imaging error using a heart rate interval may include: measuring T1 of a stand-alone phantom for correcting the error; obtaining a T1 map generated by mapping a recovery time according to a reference recovery rate of protons in heart tissues of a subject inverted by a radio frequency (RF) pulse in pixel units into a two-dimensional space; calculating a correction function based on the measured T1 of the phantom; and correcting an error of the T1 map based on the calculated correction function.

In the measuring of the T1, first T1 of the phantom may be measured using a modified look-locker inversion recovery (MOLLI) sequence, and second T1 of the phantom may be measured using an inversion recovery turbo spin echo and a MOLLI sequence.

In the calculating of the correction function, a first correction function may be calculated through multiple polynomial regression based on reference T1 and the second T1 of the phantom, and the reference T1 may be a ground-truth that becomes a reference of the measured T1 of the phantom.

In the calculating of the correction function, a second correction function may be calculated through multiple polynomial regression based on the reference T1 and the first T1 of the phantom.

In the calculating of the correction function, a third correction function may be calculated through multiple polynomial regression based on the first T1 and the second T1.

In the calculating of the correction function, the second correction functions and the third correction functions may be calculated by dividing correction coefficients according to the heart rate interval (R-R interval (RRI)).

In the correcting of the error, the T1 map may be corrected pixel-by-pixel based on the correction function.

In the correcting of the error, the error of the T1 map may be corrected using at least one of the first correction function, and the second correction function and the third correction function of which the correction coefficients are determined according to the heart rate interval of the subject.

According to another aspect of the present invention, an apparatus for correcting a magnetic resonance imaging error using a heart rate interval may include: a T1 measuring unit measuring T1 of a stand-alone phantom for correcting the error; a T1 map obtaining unit obtaining a T1 map generated by mapping a recovery time according to a reference recovery rate of protons in heart tissues of a subject inverted by a radio frequency (RF) pulse in pixel units into a two-dimensional space; a correction function calculating unit calculating a correction function based on the measured T1 of the phantom; and an error correcting unit correcting an error of the T1 map based on the calculated correction function.

The T1 measuring unit may measure first T1 of the phantom using a modified look-locker inversion recovery (MOLLI) sequence, and measure second T1 of the phantom using an inversion recovery turbo spin echo and a MOLLI sequence.

The correction function calculating unit may calculate a first correction function through multiple polynomial regression based on reference T1 and the second T1 of the phantom, and the reference T1 may be a ground-truth that becomes a reference of the measured T1 of the phantom.

The correction function calculating unit may calculate a second correction function through multiple polynomial regression based on the reference T1 and the first T1 of the phantom.

The correction function calculating unit may calculate a third correction function through multiple polynomial regression based on the first T1 and the second T1.

The correction function calculating unit may calculate the second correction functions and the third correction functions by dividing correction coefficients according to the heart rate interval (R-R interval (RRI)).

The error correcting unit may correct the T1 map pixel-by-pixel based on the correction function.

The error correcting unit may correct the error of the T1 map using at least one of the first correction function, and the second correction function and the third correction function of which the correction coefficients are determined according to the heart rate interval of the subject.

BRIEF DESCRIPTION OF DRAWINGS

The above and other aspects, features, and advantages of the present disclosure will be more clearly understood from the following detailed description taken in conjunction with the accompanying drawings, in which.

DETAILED DESCRIPTION

Figure 1:
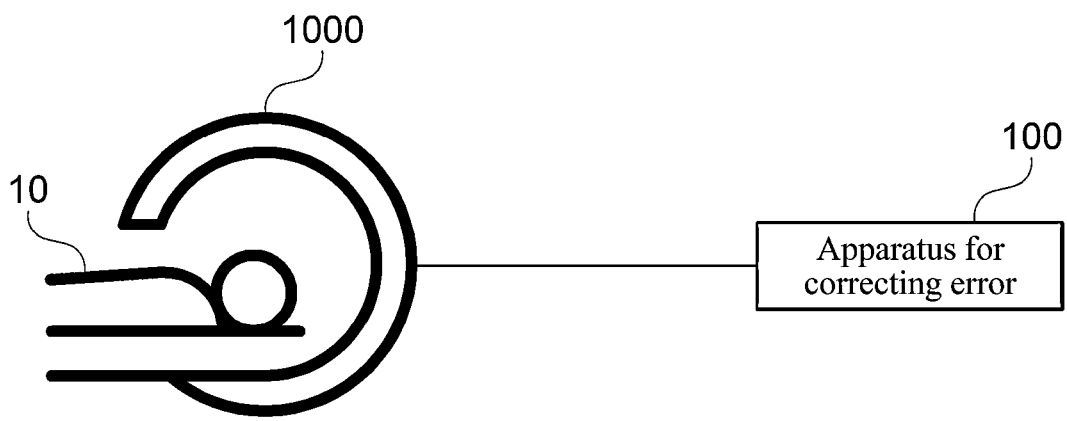
FIG. 1 is a schematic view illustrating an apparatus for collecting a magnetic resonance imaging error using a heart rate interval according to an embodiment of the present invention.

The following description exemplifies only a principle of the present invention. Therefore, those skilled in the art may implement the principle of the present invention and invent various apparatuses included in the spirit and scope of the present invention although not clearly described or illustrated in the present specification. In addition, it is to be understood that all conditional terms and embodiments mentioned in the present specification are obviously intended only to allow those skilled in the art to understand a concept of the present invention in principle, and the present invention is not limited to embodiments and states particularly mentioned as such.

The objects, features, and advantages described above will become more obvious from the following detailed description provided in relation to the accompanying drawings. Therefore, those skilled in the art to which the present invention pertains may easily practice the technical spirit of the present invention.

Further, in describing the present invention, in the case in which it is determined that a detailed description of the well-known technology related to the present invention may unnecessarily make the gist of the present invention unclear, it will be omitted. Hereinafter, embodiments of the present invention will be described in detail with reference to the accompanying drawings.

Magnetic resonance imaging (MRI) may calculate recovery times according to components by dividing components in a recovery process recovered in an exponential curve form after inversing atoms longitudinally magnetized by a magnetic field using an inversion recovery radio frequency (RF) pulse. An MRI signal is obtained by scanning a signal generated from a subject in a k-space, and an MRI image is obtained by converting the obtained MRI signal.

Specifically, features for each component of self-recovery may be weighted by adjusting, for example, a time to repetition (TR) and a time to echo (TE) as variables for an applied RF pulse.

In this case, the TR refers to a repetition time of the RF pulse. The TR refers to a time interval at which an RF pulse used to obtain a resonance signal is generated, and mainly determines an amount of longitudinal relaxation (spin-lattice interaction).

The TE is a signal generation time, and refers to a time from a point in time when the RF pulse is output to a point in time when an echo signal is obtained. The TE determines a degree (spin-spin interaction) of dispersion (dephasing) of a spin recovered onto a transverse plane.

In this case, T1 (relaxation time) is defined as a time until average magnetization of 63% of an initial state is recovered in a longitudinal direction after the RF pulse is injected and inversed in the vertical axis direction.

T2 is defined as a time it takes for average magnetization in a transverse plane to decrease up to 37% of the initial state by dephasing.

That is, a T1-weighted image or a T2-weighted image may be generated by measuring the times described above by varying the TR and the TE of the RF pulse.

Specifically, a method for correcting an error of a T1 map generated as the T1-weighted image using a heart rate will be described in the present invention.

A more detailed description will be provided with reference to FIG. 1.

FIG. 1 is a schematic view illustrating a system for collecting a magnetic resonance imaging error using a heart rate interval according to an embodiment of the present invention.

Referring to FIG. 1, an apparatus 100 for correcting an error performing a method for correcting a magnetic resonance imaging error using a heart rate according to the present embodiment may be configured in conjunction with a magnetic resonance imaging (MRI) apparatus 1000 or may be configured as a part of the MRI apparatus 1000.

The MRI apparatus 1000 applies a magnetic field and a radio frequency (RF) pulse to a subject (or a person to be photographed) 10, and extracts features in a recovery process after magnetization and inversion of hydrogen atoms in a specific axial direction, as described above. An MRI image using the signal received during the recovery process is generated to make non-invasive image obtainment and diagnosis possible.

Specifically, the MRI apparatus 1000 may calculate a T1 recovery time according to a recovery rate in a spin-lattice recovery process recovered in an exponential curve form after inverting atoms longitudinally magnetized according to a direction of a magnetic field using an inversion recovery RF pulse. In addition, a T1 value generated from the heart of the subject 10 may be scanned in a k-space to obtain an MRI signal, and the acquired MRI signal may be mapped in pixel units to generate a T1 map.

The apparatus 100 for correcting an error is an apparatus for correcting an error of the T1 map, and may measure T1 of a general type of stand-alone phantom through the MRI apparatus 1000 and calculate a correction function based on T1 of the phantom. Here, the stand-alone phantom is a composition in which NiCl2 and Agarose are mixed with each other at various concentrations so that ranges of T1 and T2 values in the myocardium are obtained, and is a phantom positioned alone in the MRI apparatus 1000 and designed to measure T1, unlike a conventional attachable phantom attached to the subject 10 and entering the MRI apparatus 1000 together with the subject 10. In the present invention, T1MES phantom of 'T1 mapping performance and measurement repeatability: results from the multi-national T1 mapping standardization phantom program (T1MES))' published in the JCMR journal in 2016 is used.

In addition, the apparatus 100 for correcting an error may correct the error of the T1 map of the subject 10 based on the calculated correction function.

Figure 2:
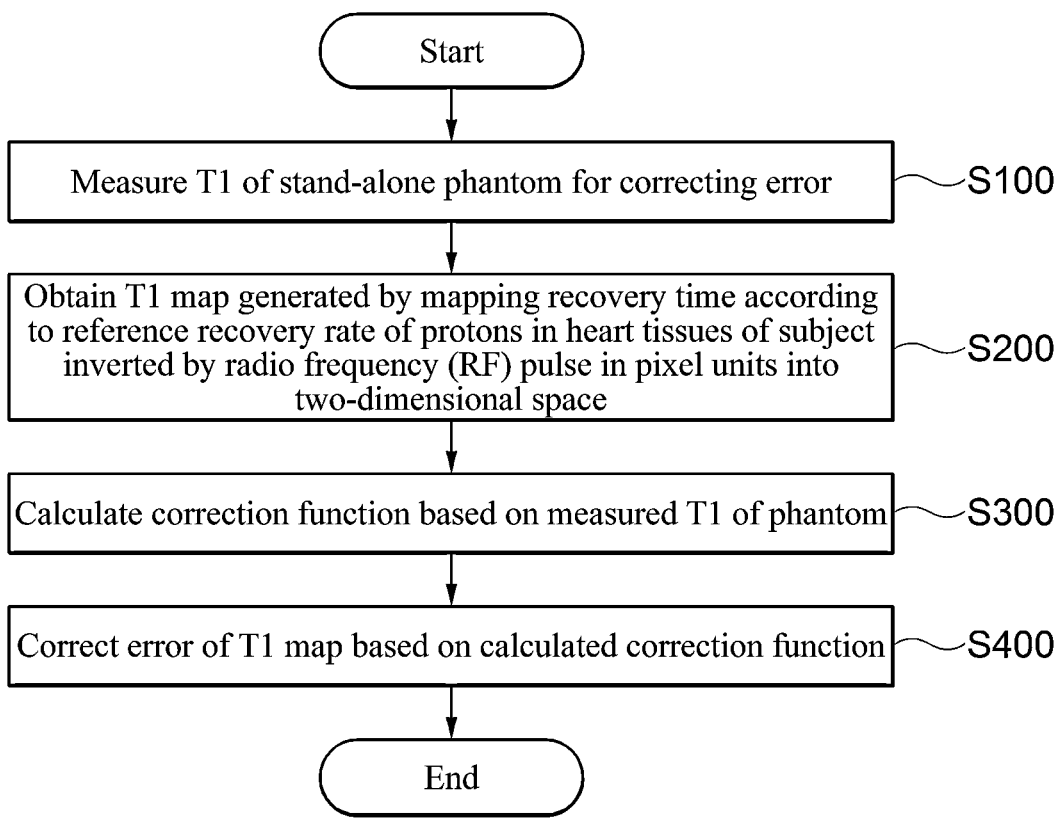
FIG. 2 is a flowchart illustrating a method for correcting a magnetic resonance imaging error according to an embodiment of the present invention.

Hereinafter, a method for correcting a magnetic resonance imaging error using a heart rate according to the present embodiment will be described in more detail with reference to FIG. 2.

The apparatus 100 for correcting an error may measure T1 of a stand-alone phantom for correcting the error through the MRI apparatus 1000 (S100).

Specifically, the apparatus 100 for correcting an error may measure first T1 of the phantom according to a heart rate interval using a modified look-locker inversion recovery (MOLLI) sequence.

Hereinafter, a method for measuring the first T1 of the phantom using the MOLLI sequence will be described with reference to FIGS. 3 and 4.

Figure 3:
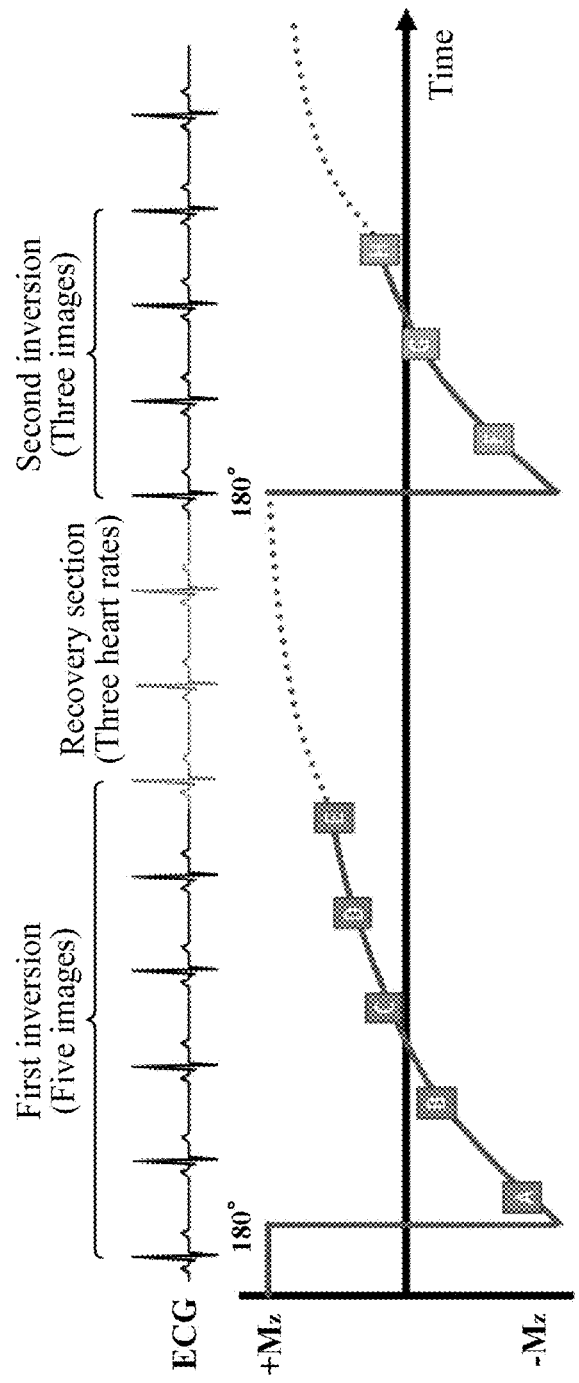
FIGS. 3 and 4 are illustrative views illustrating a method for measuring first T1 of a phantom using a modified look-locker inversion recovery (MOLLI) sequence according to an embodiment of the present invention.

Referring to FIG. 3, the apparatus 100 for correcting an error may obtain a plurality of images according to heart rate interval and RF pulse synchronization. Here, in the case of the heart, the heart rate interval may be measured by measuring an electrical signal generated from the heart called an electrocardiogram (ECG). For example, a heart rate cycle may be determined based on a specific waveform in the ECG signal. Specifically, an R wave representing the highest point in a QRS group may be used to obtain an intermediate map in units of an R-R interval defined as an interval between the R wave and the R wave of the next signal, thereby minimizing an influence of the heart rate to obtain an image.

Specifically, as illustrated in FIG. 3, after the RF pulse is applied, a plurality of signals at a specific point in time in the R-R interval may be measured.

When first inversion occurs after a first RF pulse is applied, a plurality of partial images may be acquired by repeatedly measuring recovery signals in a longitudinal direction of atoms in heart tissues according to the R-R interval.

In this case, the number (five) of obtained images may be predetermined, a second RF pulse is applied on the premise that the atoms have been recovered through a recovery section after the images are obtained, and when second inversion occurs, a plurality of (three) partial images may be obtained as an intermediate map for generating T1 to the R-R interval.

Figure 4:
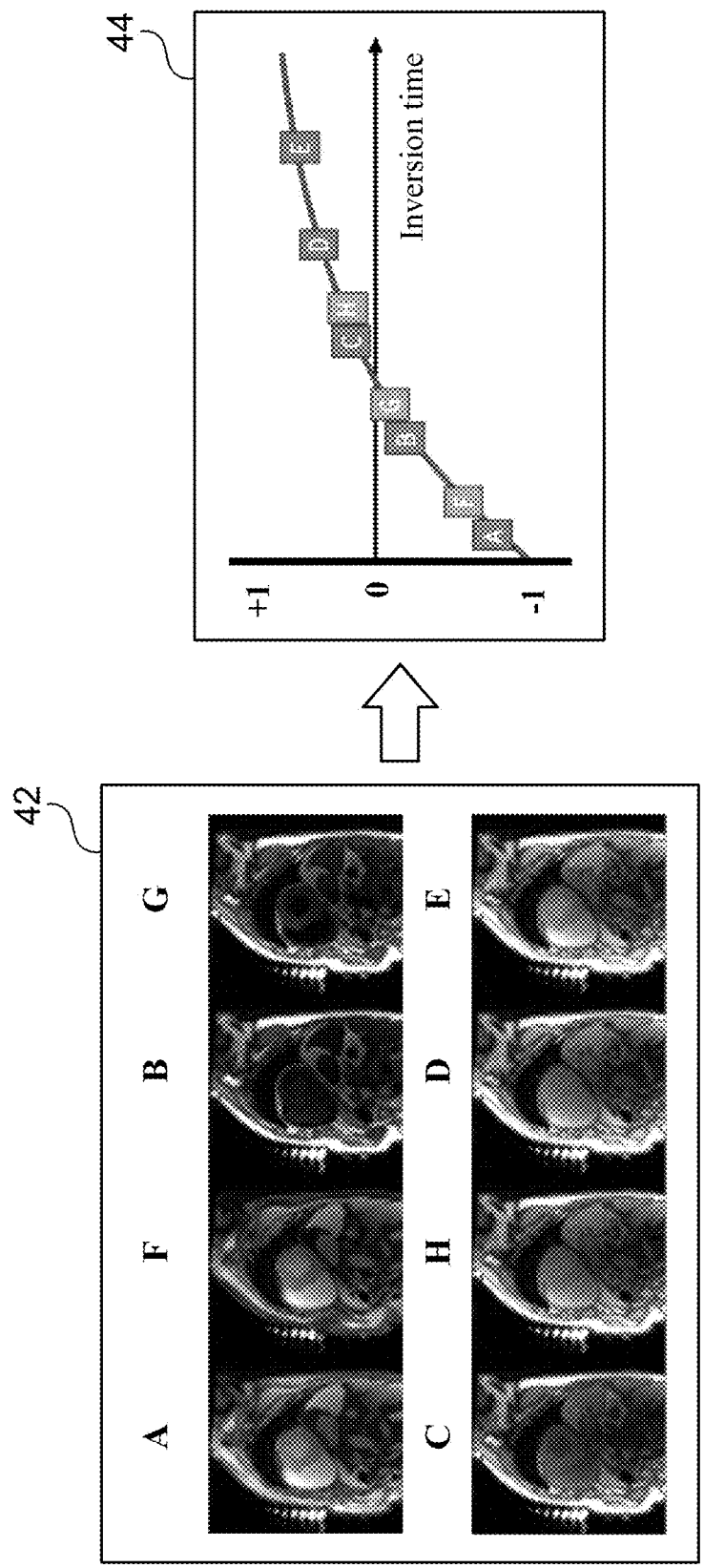

In addition, the apparatus 100 for correcting an error may map recovery times of heart tissues in eight (a plurality of) partial images A to E 42 obtained as illustrated in FIG. 4 in pixel units, and fit the recovery times to a normalized curve 44.

Hydrogen atoms are rotated from +M0, which is the equilibrium state, by 180° to be inversed to −M0, using an inversion recovery (IR) pulse. Thereafter, an inversion time (TI) is adjusted at a time interval at which image obtainment is started after photographing. In this case, a degree at which inverted hydrogen atoms are recovered to +M0 and a contrast of MRI images vary according to the TI.

That is, a longitudinal recovery amount after the inversion of hydrogen atoms in the heart tissues may be measured in pixel units in the plurality of partial images, and may be fitted in the form of an exponential function.

A curve for curve fitting may be defined by a model of three-parameters (A, B, and T1). The curve has a time value t according to T1* as an input of an exponential function, and a signal intensity y(t) according to the time t is defined by the following Equation 1.

$$y(t)=A-B\cdot\exp(-t/T_1^*)$$ [Equation 1]

In addition, T1 may be calculated by applying the following Equation 2.

$$T_1=T_1^*\cdot((B/A)-1)$$ [Equation 2]

With the above Equations, the apparatus 100 for correcting an error may measure the first T1 of the phantom according to the heart rate interval.

In addition, in the measuring (S100) of the T1, the apparatus 100 for correcting an error may measure second T1 of the phantom according to the heart rate interval using an inversion recovery turbo spin echo (IR-TSE) and a MOLLI sequence. Here, the inversion recovery turbo spin echo is a method for filling different k-spaces by obtaining echoes having a plurality of different phase codes during one TR.

That is, in the measuring (S100) of the T1, the first T1 of the phantom may be measured using the modified look-locker inversion recovery (MOLLI) sequence, and the second T1 of the phantom may be measured according to the heart rate interval using the inversion recovery turbo spin echo and the MOLLI sequence.

Next, the apparatus 100 for correcting an error may obtain a T1 map generated by mapping a recovery time according to a reference recovery rate of protons in the heart tissues of the subject inverted by the RF pulse in pixel units into a two-dimensional space, from the MRI apparatus 1000 (S200). In addition, the apparatus 100 for correcting an error may directly generate the T1 map through the MRI apparatus 1000.

Next, the apparatus 100 for correcting an error may calculate three correction functions based on the measured T1 of the phantom (S300).

Specifically, the apparatus 100 for correcting an error may calculate a first correction function through multiple polynomial regression based on reference T1 and the second T1 of the phantom, calculate a second correction function through multiple polynomial regression based on the reference T1 and the first T1 of the phantom, and calculate a third correction function through multiple polynomial regression based on the first T1 and the second T1. Here, the reference T1 refers to a ground-truth that becomes a reference of the measured T1 of the phantom.

That is, in order for the apparatus 100 for correcting an error to generate the correction functions, the first correction function may use a gold-standard T1 map-based calibration (GC), the second correction function may use a MOLLI T1 map-based calibration (MC), and the third calibration function may use an internal reference-based calibration (IC).

In addition, the apparatus 100 for correcting an error may arbitrarily set a heart rate interval of the subject, and calculate each of the second correction function and the third correction function depending on whether or not the heart rate interval (R-R interval (RRI)) is considered.

For example, the apparatus 100 for correcting an error may subdivide the second correction function and the third correction function into a case where the heart rate interval is considered and a case where the heart rate interval is not considered (static RRI, 900 ms), respectively, as illustrated in Table 1

TABLE 1

| Method | RRI [ms] | Input Source | Calibration Model | Index |
|---|---|---|---|---|
| Gold-standard T1 map based calibration (GC) | N/A | $x = T1_{GS}$ $y = T1_{GT}$ | $y = cx + d$ $y = bx^2 + cx + d$ $y = ax^3 + bx^2 + cx + d$ | $GC_1$ $GC_2$ $GC_3$ |
| MOLLI T1 map based calibration (MC) | 900 | $x = T1_{ML(S)}$ $y = T1_{GT}$ | $y = cx + d$ $y = bx^2 + cx + d$ $y = ax^3 + bx^2 + cx + d$ | $MC_{1S}$ $MC_{2S}$ $MC_{3S}$ |
| | Various | $x = T1_{ML(V)}$ $y = T1_{GT}$ | $y = cx + d$ $y = bx^2 + cx + d$ $y = ax^3 + bx^2 + cx + d$ | $MC_{1V}$ $MC_{2V}$ $MC_{3V}$ |
| Internal Reference based calibration (IC) | 900 | $x = T1_{ML(S)}$ $y = T1_{GS}$ | $y = cx + d$ $y = bx^2 + cx + d$ $y = ax^3 + bx^2 + cx + d$ | $IC_{1S}$ $IC_{2S}$ $IC_{3S}$ |
| | Various | $x = T1_{ML(V)}$ $y = T1_{GT}$ | $y = cx + d$ $y = bx^2 + cx + d$ $y = ax^3 + bx^2 + cx + d$ | $IC_{1V}$ $IC_{2V}$ $IC_{3V}$ |

In this case, the apparatus 100 for correcting an error may calculate the second correction functions and the third correction functions using the first T1 corresponding to each heart rate interval.

For example, in a case where the heart rate interval is subdivided at intervals of 100 ms in the range of 700 to 1100 ms, the apparatus 100 for correcting an error may calculate the second correction functions having correction coefficients as illustrated in Table 2 using the first T1 corresponding to each heart rate interval.

Table 2 is a table illustrating correction coefficients corresponding to RRIs of a myocardial native T1 map before injection of a contrast medium for the MOLLI T1 map-based calibration.

TABLE 2

| Method | | | Coefficient of Calibration function | | | |
|---|---|---|---|---|---|---|
| Institution | Index | RRI[ms] | a | b | c | d |
| A | MC1 | 700 | 0 | 0 | 1.051E+00 | −3.304E+00 |
| | | 800 | 0 | 0 | 1.043E+00 | 1.156E+00 |
| | | 900 | 0 | 0 | 1.035E+00 | 5.357E+00 |
| | | 1000 | 0 | 0 | 1.029E+00 | 7.576E+00 |
| | | 1100 | 0 | 0 | 1.026E+00 | 9.989E+00 |
| | MC2 | 700 | 0 | −1.252E−04 | 1.296E+00 | −8.470E+01 |
| | | 800 | 0 | −1.313E−04 | 1.302E+00 | −8.486E+01 |
| | | 900 | 0 | −1.376E−04 | 1.308E+00 | −8.543E+01 |
| | | 1000 | 0 | −1.418E−04 | 1.312E+00 | −8.678E+01 |
| | | 1100 | 0 | −1.481E−04 | 1.322E+00 | −8.903E+01 |
| | MC3 | 700 | −1.995E−07 | 5.045E−04 | 7.314E−01 | 4.388E+01 |
| | | 800 | −1.881E−07 | 4.656E−04 | 7.639E−01 | 3.777E+01 |
| | | 900 | −1.804E−07 | 4.381E−04 | 7.870E−01 | 3.356E+01 |
| | | 1000 | −1.790E−07 | 4.324E−04 | 7.900E−01 | 3.280E+01 |
| | | 1100 | −1.821E−07 | 4.380E−04 | 7.875E−01 | 3.350E+01 |
| B | MC1 | 700 | 0 | 0 | 1.054E+00 | −9.291E+00 |
| | | 800 | 0 | 0 | 1.046E+00 | −4.517E+00 |
| | | 900 | 0 | 0 | 1.036E+00 | 9.215E−01 |
| | | 1000 | 0 | 0 | 1.032E+00 | 4.097E+00 |
| | | 1100 | 0 | 0 | 1.031E+00 | 5.195E+00 |
| | MC2 | 700 | 0 | −1.057E−04 | 1.261E+00 | −7.798E+01 |
| | | 800 | 0 | −1.111E−04 | 1.264E+00 | −7.724E+01 |
| | | 900 | 0 | −1.274E−04 | 1.289E+00 | −8.356E+01 |
| | | 1000 | 0 | −1.314E−04 | 1.293E+00 | −8.317E+01 |
| | | 1100 | 0 | −1.378E−04 | 1.305E+00 | −8.657E+01 |
| | MC3 | 700 | −1.895E−07 | 4.900E−04 | 7.278E−01 | 4.350E+01 |
| | | 800 | −1.895E−07 | 4.878E−04 | 7.260E−01 | 4.552E+01 |
| | | 900 | −1.765E−07 | 4.355E−04 | 7.788E−01 | 3.333E+01 |
| | | 1000 | −1.770E−07 | 4.342E−04 | 7.808E−01 | 3.422E+01 |
| | | 1100 | −1.843E−07 | 4.525E−04 | 7.697E−01 | 3.622E+01 |
| C | MC1 | 700 | 0 | 0 | 1.018E+00 | 7.368E+00 |
| | | 800 | 0 | 0 | 1.010E+00 | 1.242E+01 |
| | | 900 | 0 | 0 | 1.002E+00 | 1.522E+01 |
| | | 1000 | 0 | 0 | 9.961E−01 | 1.939E+01 |
| | | 1100 | 0 | 0 | 9.937E−01 | 1.949E+01 |

TABLE 2-continued

| Institution | Method Index | RRI[ms] | Coefficient of Calibration function | | | |
|---|---|---|---|---|---|---|
| | | | a | b | c | d |
| | MC2 | 700 | 0 | −1.277E−04 | 1.274E+00 | −7.902E+01 |
| | | 800 | 0 | −1.318E−04 | 1.276E+00 | −7.714E+01 |
| | | 900 | 0 | −1.360E−04 | 1.279E+00 | −7.820E+01 |
| | | 1000 | 0 | −1.447E−04 | 1.291E+00 | −8.076E+01 |
| | | 1100 | 0 | −1.488E−04 | 1.298E+00 | −8.424E+01 |
| | MC3 | 700 | −1.684E−07 | 4.165E−04 | 7.760E−01 | 3.601E+01 |
| | | 800 | −1.551E−07 | 3.721E−04 | 8.121E−01 | 2.994E+01 |
| | | 900 | −1.530E−07 | 3.638E−04 | 8.172E−01 | 2.870E+01 |
| | | 1000 | −1.469E−07 | 3.374E−04 | 8.444E−01 | 2.294E+01 |
| | | 1100 | −1.401E−07 | 3.126E−04 | 8.691E−01 | 1.579E+01 |

In addition, in a case where the heart rate interval is not considered, the apparatus 100 for correcting an error may calculate correction functions having correction coefficients illustrated in Table 3 using T1 corresponding to a heart rate interval (RRI) of 900 ms.

Table 3 is a table illustrating correction coefficients for a myocardial native T1 map before injection of a contrast medium and a post T1 map after the injection of the contrast medium at heart rate intervals of 900 ms.

TABLE 3

| Calibration Method | T1 map | Method Index | Institution | Coefficient of Calibration function | | | |
|---|---|---|---|---|---|---|---|
| | | | | a | b | c | d |
| Gold-Standard T1 map based Calibration (GC) | IR-TSE | GC1 | A | 0 | 0 | 9.770E−01 | 7.528E+00 |
| | | | B | 0 | 0 | 9.808E−01 | 5.505E+00 |
| | | | C | 0 | 0 | 9.206E−01 | 2.295E+01 |
| | | GC2 | A | 0 | −6.234E−06 | 9.897E−01 | 3.284E+00 |
| | | | B | 0 | −7.538E−06 | 9.961E−01 | 3.755E−01 |
| | | | C | 0 | −3.446E−05 | 9.944E−01 | −2.735E+00 |
| | | GC3 | A | 5.520E−08 | −1.834E−04 | 1.151E+00 | −3.409E+01 |
| | | | B | 4.178E−08 | −1.415E−04 | 1.118E+00 | −2.785E+01 |
| | | | C | 5.046E−08 | −2.054E−04 | 1.158E+00 | −4.214E+01 |
| MOLLI T1 map based Calibration (MC) | Native T1 | MC1 | A | 0 | 0 | 1.035E+00 | 5.357E+00 |
| | | | B | 0 | 0 | 1.036E+00 | 9.215E−01 |
| | | | C | 0 | 0 | 1.002E+00 | 1.522E+01 |
| | | MC2 | A | 0 | −1.376E−04 | 1.308E+00 | −8.543E+01 |
| | | | B | 0 | −1.274E−04 | 1.289E+00 | −8.356E+01 |
| | | | C | 0 | −1.360E−04 | 1.279E+00 | −7.820E+01 |
| | | MC3 | A | −1.804E−07 | 4.381E−04 | 7.870E−01 | 3.356E+01 |
| | | | B | −1.765E−07 | 4.355E−04 | 7.788E−01 | 3.333E+01 |
| | | | C | −1.530E−07 | 3.638E−04 | 8.172E−01 | 2.870E+01 |
| | Post T1 | MC1 | A | 0 | 0 | 1.180E+00 | −5.357E+01 |
| | | | B | 0 | 0 | 1.179E+00 | −5.593E+01 |
| | | | C | 0 | 0 | 1.146E+00 | −4.305E+01 |
| | | MC2 | A | 0 | −9.653E−05 | 1.355E+00 | −1.093E+02 |
| | | | B | 0 | −7.223E−05 | 1.310E+00 | −9.752E+01 |
| | | | C | 0 | −1.034E−04 | 1.338E+00 | −1.049E+02 |
| | | MC3 | A | −4.142E−07 | 1.108E−03 | 3.479E−01 | 1.104E+02 |
| | | | B | −4.002E−07 | 1.089E−03 | 3.407E−01 | 1.137E+02 |
| | | | C | −3.633E−07 | 9.763E−04 | 4.180E−01 | 9.839E+01 |
| Internal Reference based Calibration (IC) | Native T1 | IC1 | A | 0 | 0 | 1.059E+00 | −1.736E+00 |
| | | | B | 0 | 0 | 1.056E+00 | −4.362E+00 |
| | | | C | 0 | 0 | 1.089E+00 | −8.298E+00 |
| | | IC2 | A | 0 | −1.428E−04 | 1.342E+00 | −9.595E+01 |
| | | | B | 0 | −1.288E−04 | 1.311E+00 | −8.982E+01 |
| | | | C | 0 | −1.173E−04 | 1.327E+00 | −8.886E+01 |
| | | IC3 | A | −2.507E−07 | 6.571E−04 | 6.182E−01 | 6.938E+01 |
| | | | B | −2.309E−07 | 6.078E−04 | 6.443E−01 | 6.317E+01 |
| | | | C | −2.432E−07 | 6.768E−04 | 5.938E−01 | 8.096E+01 |
| | Post T1 | IC1 | A | 0 | 0 | 1.207E+00 | −6.174E+01 |
| | | | B | 0 | 0 | 1.201E+00 | −6.205E+01 |
| | | | C | 0 | 0 | 1.244E+00 | −7.093E+01 |
| | | IC2 | A | 0 | −1.012E−04 | 1.390E+00 | −1.202E+02 |
| | | | B | 0 | −7.230E−05 | 1.332E+00 | −1.037E+02 |
| | | | C | 0 | −7.316E−05 | 1.379E+00 | −1.147E+02 |
| | | IC3 | A | −5.079E−07 | 1.376E−03 | 1.551E−01 | 1.492E+02 |
| | | | B | −4.709E−07 | 1.294E−03 | 1.921E−01 | 1.448E+02 |
| | | | C | −4.907E−07 | 1.385E−03 | 1.372E−01 | 1.599E+02 |

That is, the apparatus 100 for correcting an error may calculate the second correction functions and the third correction functions by subdividing the correction coefficients according to the heart rate interval (RRI).

Meanwhile, the apparatus 100 for correcting an error may calculate the second correction functions and the third correction functions by subdividing the correction coefficients according to a heart rate cycle.

For example, the apparatus 100 for correcting an error may set the heart rate cycle of the subject 10 to 50, 60, 70, 80, and 90 bpm (beat per minute), photograph the subject, and calculate the second correction functions and the third correction functions by dividing the correction coefficients according to the heart rate cycle.

Next, the apparatus 100 for correcting an error may correct an error of the T1 map based on the calculated correction function (S400).

Specifically, the apparatus 100 for correcting an error may correct the T1 map pixel-by-pixel based on the correction function. In this case, the apparatus 100 for correcting an error may use at least one of the first correction function, and the second correction function and the third correction function of which the correction coefficients are determined according to the heart rate interval of the subject.

For example, the apparatus 100 for correcting an error may correct the T1 map using a correction function as represented in the following Equation 3.

$$y = a \cdot x^2 + b \cdot x^2 + c \cdot x + d \quad \text{[Equation 3]}$$

In Equation 3, x is an uncorrected T1 value, y is a corrected T1 value, and a, b, c, and d are correction coefficients and may be determined according to the heart rate interval of the subject as illustrated in Table 2 or Table 3.

That is, in the correcting (S400) of the error, the apparatus 100 for correcting an error may correct the error of the T1 map using at least one of the first correction function, and the second correction function and the third correction function of which the correction coefficients are determined according to the heart rate interval of the subject.

Hereinafter, the apparatus 100 for correcting an error performing the method for correcting an error according to the present embodiment will be described with reference to FIG. 5.

Figure 5:
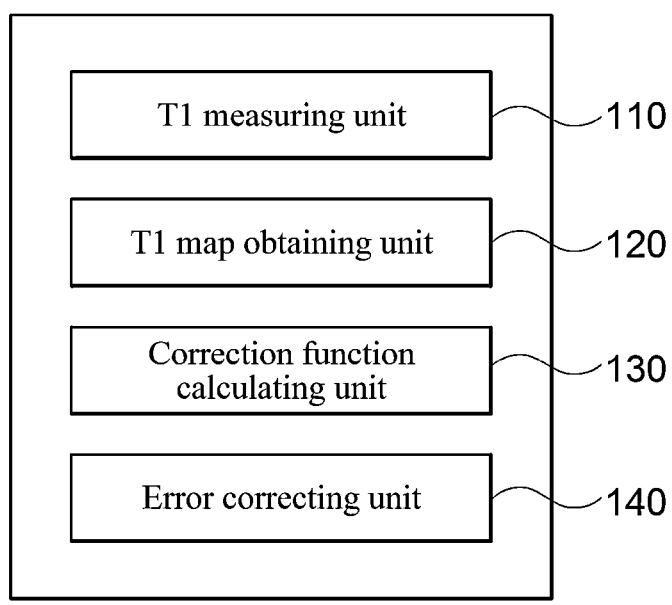
FIG. 5 is a block diagram illustrating components of an apparatus for correcting an error according to an embodiment of the present invention.

Referring to FIG. 5, the apparatus 100 for correcting an error may include a T1 measuring unit 110, a T1 map obtaining unit 120, a correction function calculating unit 130, and an error correcting unit 140.

The T1 measuring unit 110 may measure or obtain T1 of a stand-alone phantom for correcting the error through the MRI apparatus 1000.

The T1 measuring unit 110 may measure the first T1 of the phantom using the modified look-locker inversion recovery (MOLLI) sequence, and measure or obtain the second T1 of the phantom using the inversion recovery turbo spin echo and the MOLLI sequence.

In addition, the T1 map obtaining unit 120 may obtain the T1 map generated by mapping the recovery time according to the reference recovery rate of the protons in the heart tissues of the subject inverted by the RF pulse in pixel units into the two-dimensional space, through the MRI apparatus 1000.

The correction function calculating unit 130 may calculate the correction function based on the measured T1 of the phantom.

Specifically, the correction function calculating unit 130 may calculate the first correction function through the multiple polynomial regression based on the reference T1 and the second T1 of the phantom, calculate the second correction function through the multiple polynomial regression based on the reference T1 and the first T1 of the phantom, and calculate the third correction function through the multiple polynomial regression based on the first T1 and the second T1.

In this case, the correction function calculating unit 130 may calculate the second correction functions and the third correction functions by subdividing the correction coefficients according to the heart rate interval (RRI).

The error correcting unit 140 may correct the error of the T1 map based on the calculated correction function.

Specifically, the error correcting unit 140 may correct the T1 map pixel-by-pixel based on the correction function.

In this case, the error correcting unit 140 may correct the error of the T1 map using at least one of the first correction function, and the second correction function and the third correction function of which the correction coefficients are determined according to the heart rate interval of the subject.

As described above, according to the present invention, the error may be accurately corrected by using the stand-alone phantom instead of the attachable phantom.

In addition, the present invention may have a high correction success rate in an actual clinical environment by subdividing the correction function in consideration of the heart rate interval.

Furthermore, various embodiments described herein may be implemented in computer-readable recording medium using, for example, software, hardware, or a combination thereof.

According to a hardware implementation, embodiments described herein may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electric units for performing other functions. In some cases, embodiments described in the present specification may be implemented as a control module itself.

According to a software implementation, embodiments such as procedures and functions described in the present specification may be implemented as separate software modules. Each of the software modules may perform one or more functions and operations described in the present specification. A software code may be implemented as a software application written in a suitable programming language. The software code may be stored in a memory module and executed by a control module.

The technical spirit of the present invention has been described only by way of example hereinabove, and the present invention may be variously modified, altered, and substituted by those skilled in the art to which the present invention pertains without departing from essential features of the present invention.

Accordingly, embodiments disclosed in the present invention and the accompanying drawings are provided in order to describe the technical spirit of the present invention rather than limiting the technical spirit of the present invention, and the scope of the present invention is not limited by these embodiments and the accompanying drawings. The scope of the present invention should be interpreted by the following claims and it should be interpreted that all spirits equivalent to the following claims fall within the scope of the present invention.

What is claimed is:

1. A method for correcting a magnetic resonance imaging error using a heart rate interval, comprising:
   measuring T1 of a stand-alone phantom for correcting the error;
   obtaining a T1 map generated by mapping a recovery time according to a reference recovery rate of protons in heart tissues of a subject inverted by a radio frequency (RF) pulse in pixel units into a two-dimensional space;
   calculating a correction function based on the measured T1 of the phantom; and
   correcting an error of the T1 map based on the calculated correction function,
   wherein in the measuring of the T1, first T1 of the phantom is measured using a modified look-locker inversion recovery (MOLLI) sequence, and second T1 of the phantom is measured using an inversion recovery turbo spin echo and a MOLLI sequence, and
   wherein in the calculating of the correction function, a first correction function is calculated through multiple polynomial regression based on reference T1 and the second T1 of the phantom, and the reference T1 is a ground-truth that becomes a reference of the measured T1 of the phantom.

2. The method of claim 1, wherein in the calculating of the correction function, a second correction function is calculated through multiple polynomial regression based on the reference T1 and the first T1 of the phantom.

3. The method of claim 1, wherein in the calculating of the correction function, a third correction function is calculated through multiple polynomial regression based on the first T1 and the second T1.

4. The method of claim 2, wherein in the calculating of the correction function, the second correction functions and the third correction functions are calculated by dividing correction coefficients according to the heart rate interval (R-R interval (RRI)).

5. The method of claim 4, wherein in the correcting of the error, the T1 map is corrected pixel-by-pixel based on the correction function.

6. The method of claim 5, wherein in the correcting of the error, the error of the T1 map is corrected using at least one of the first correction function, and the second correction function and the third correction function of which the correction coefficients are determined according to the heart rate interval of the subject.

7. An apparatus for correcting a magnetic resonance imaging error using a heart rate interval, comprising:
   a T1 measuring unit measuring T1 of a stand-alone phantom for correcting the error;
   a T1 map obtaining unit obtaining a T1 map generated by mapping a recovery time according to a reference recovery rate of protons in heart tissues of a subject inverted by a radio frequency (RF) pulse in pixel units into a two-dimensional space;
   a correction function calculating unit calculating a correction function based on the measured T1 of the phantom; and
   an error correcting unit correcting an error of the T1 map based on the calculated correction function,
   wherein the T1 measuring unit measures first T1 of the phantom using a modified look-locker inversion recovery (MOLLI) sequence, and measures second T1 of the phantom using an inversion recovery turbo spin echo and a MOLLI sequence, and
   wherein the correction function calculating unit calculates a first correction function through multiple polynomial regression based on reference T1 and the second T1 of the phantom, and the reference T1 is a ground-truth that becomes a reference of the measured T1 of the phantom.

8. The apparatus of claim 7, wherein the correction function calculating unit calculates a second correction function through multiple polynomial regression based on the reference T1 and the first T1 of the phantom.

9. The apparatus of claim 7, wherein the correction function calculating unit calculates a third correction function through multiple polynomial regression based on the first T1 and the second T1.

10. The apparatus of claim 8, wherein the correction function calculating unit calculates the second correction functions and the third correction functions by dividing correction coefficients according to the heart rate interval (R-R interval (RRI)).

11. The apparatus of claim 10, wherein the error correcting unit corrects the T1 map pixel-by-pixel based on the correction function.

12. The apparatus of claim 11, wherein the error correcting unit corrects the error of the T1 map using at least one of the first correction function, and the second correction function and the third correction function of which the correction coefficients are determined according to the heart rate interval of the subject.

13. A computer-readable recording medium in which a computer program for executing the method for correcting a magnetic resonance imaging error using a heart rate interval, comprising:
   measuring T1 of a stand-alone phantom for correcting the error;
   obtaining a T1 map generated by mapping a recovery time according to a reference recovery rate of protons in heart tissues of a subject inverted by a radio frequency (RF) pulse in pixel units into a two-dimensional space;
   calculating a correction function based on the measured T1 of the phantom; and
   correcting an error of the T1 map based on the calculated correction function,
   wherein in the measuring of the T1, first T1 of the phantom is measured using a modified look-locker inversion recovery (MOLLI) sequence, and second T1 of the phantom is measured using an inversion recovery turbo spin echo and a MOLLI sequence, and
   wherein in the calculating of the correction function, a first correction function is calculated through multiple polynomial regression based on reference T1 and the second T1 of the phantom, and the reference T1 is a ground-truth that becomes a reference of the measured T1 of the phantom.

14. The computer-readable recording medium of claim 13, wherein in the calculating of the correction function, the second correction functions and the third correction functions are calculated by dividing correction coefficients according to the heart rate interval (R-R interval (RRI)).

* * * * *